United States Patent [19]

Villafana

[11] Patent Number: 5,487,760
[45] Date of Patent: Jan. 30, 1996

[54] HEART VALVE PROSTHESIS INCORPORATING ELECTRONIC SENSING, MONITORING AND/OR PACING CIRCUITRY

[75] Inventor: Manuel A. Villafana, Minneapolis, Minn.

[73] Assignee: ATS Medical, Inc., Minneapolis, Minn.

[21] Appl. No.: 207,760

[22] Filed: Mar. 8, 1994

[51] Int. Cl.⁶ ........................................... A61F 2/24
[52] U.S. Cl. ........................... 623/2; 623/3; 623/11; 623/12; 623/66; 607/33; 607/119
[58] Field of Search .................. 623/2–3, 11, 12, 623/66, 900; 128/734, 739, 741, 748, 696–697, 714, 672, 675, 666, 667, 637, 774, 903; 607/9, 33, 119

[56] References Cited

U.S. PATENT DOCUMENTS

| | | |
|---|---|---|
| 3,861,387 | 1/1975 | Lawhorn . |
| 4,378,022 | 3/1983 | Suobank et al. . |
| 4,428,381 | 1/1984 | Hepp . |
| 4,458,693 | 7/1984 | Badzinski et al. . |
| 4,722,349 | 2/1988 | Baumberg . |
| 4,769,032 | 9/1988 | Steinberg ............................. 623/2 |
| 4,775,887 | 10/1988 | Tachi . |
| 5,172,698 | 12/1992 | Stanko . |
| 5,226,431 | 7/1993 | Bible et al. . |
| 5,402,794 | 4/1995 | Wahlstrand et al. ................ 128/696 |
| 5,425,373 | 6/1995 | Causey, III ......................... 128/697 |

*Primary Examiner*—Randall L. Green
*Assistant Examiner*—P. Zuttarelli
*Attorney, Agent, or Firm*—Haugen & Nikolai

[57] ABSTRACT

A heart valve prosthesis containing electronic circuitry for monitoring valve performance provides information to an implanted transceiver arranged to transmit digital or analog data transcutaneously to an external transceiver. The implanted electronics may be integrally contained within the heart valve prosthesis, or alternatively, may be separately housed in a moisture-proof container within the patient's body but external to the heart. By coupling the implanted transceiver to a pulse generator and electrode combination, electrical stimulating pulses can be applied to the heart upon command from an externally located monitor/transceiver combination.

20 Claims, 2 Drawing Sheets

HEART VALVE PROSTHESIS INCORPORATING ELECTRONIC SENSING, MONITORING AND/OR PACING CIRCUITRY

BACKGROUND OF THE INVENTION

1. Field of the Invention

This invention relates generally to an improved heart valve prosthesis, and more particularly to such a prosthesis device which may be implanted to replace a defective natural or artificial heart valve and which incorporates electronics for monitoring and telemetering operational conditions of the valve and other biodata to an external receiver, as well as for providing stimulation pulses for pacing. The improved prosthesis device of the present invention employs at least one, but preferably two or even three occluder means, each in the form of a flat or curved plate or leaflet, both functioning hemodynamically by a periodic opening and closing motion which is created through normal pumping action of the heart. The improved prosthesis device may alternatively employ multiple occluder means, such as two or three flat or curved plates, or alternatively, a ball and cage check occluder. A sensor is incorporated for detecting such things as the movement of the leaflets and a transmitter/receiver (transceiver) is incorporated for sending and receiving data and commands from an external apparatus.

2. Discussion of the Prior Art

As is well known in the art, prosthetic heart valves function essentially as check valves. Blood flow, which occurs as a result of the natural pumping action of the heart, causes periodic opening of the leaflets, with the system pressure closing the leaflets during periods of diastole when in the aortic position or during periods of systole when in the atrial-ventricular position.

A variety of prosthetic heart valves have been proposed and utilized in the past. Certain of these prosthetic devices have employed a caged ball arrangement which also function and control blood flow in response to normal pumping action of the heart. The caged-ball designs have been found objectionable from a psychologic standpoint because of the audible clicking sounds emitted as the ball is made to seat and unseat relative to the opening in the valve body. Other heart valve prostheses have employed occluders in the form of either a round disk or a pair of semi-circular and semi-elliptical plates. The latter are normally referred to as bi-leaflet valves. While various materials of construction have been employed in the past, the more recently utilized heart valve prostheses have been fabricated essentially from pyrolytic carbon.

Bi-leaflet valves normally employ a strategically designed pivot means to appropriately guide and otherwise control the motion of the leaflets as they are made to move between their open and closed dispositions. In addition, means have been provided to control or limit the extent of motion to which the leaflets are subjected during opening and closing, thereby providing an arrangement wherein the motion of the individual leaflets is carefully guided, controlled, limited and maintained.

It is further known that blood components, including those cells normally found in human blood, are extremely fragile and delicate. These cells can be damaged and/or destroyed if subjected to unusual mechanical forces. Thus, care must be taken to control the nature of the forces created during the occurrence of relative motion between the leaflets and their surrounding annular body. For example, reduction of the occurrences of rubbing contact between stationary and moving surfaces is of importance when such contact is likely to cause mechanical damage to the various cell types present in blood. The design and configuration of the heart valve prosthesis of the present invention is such that care has been taken to reduce the creation of zones or areas where blood passing through the device is exposed to substantial mechanical forces. As such, the operation of the valve of the present invention is practically noiseless and conventional acoustic techniques cannot be used to assess operational performance of such "silent" valves. Accordingly, it is desirable that some alternative method of monitoring valve performance and other physiologic parameters be incorporated in or with the valve.

SUMMARY OF THE INVENTION

The heart valve prosthesis of the present invention comprises an improvement which is particularly adapted for use as a modification of the valve described in co-pending application Ser. No. 08/122,802, filed Sep. 16, 1993 now U.S. Pat. No. 5,354,330, and entitled "HEART VALVE PROSTHESIS", the teachings of which are hereby incorporated fully by reference in this specification. It will be understood, of course, that the features of the present invention are readily adaptable for implementation in other types of valves, including other mechanical valves as well as tissue valves. In application Ser. No. 08/122,802 now U.S. Pat. No. 5,354,330, there is described a heart valve prosthesis having a generally annular body member with an interior surface defining a central passageway or lumen for blood flow therethrough. The annular body member is preferably formed from pyrolytic carbon and is provided with means for supporting a pair of pivotally moveable leaflets or occluders within the annular body in such a way that they alternately open and close under influence of the blood being pumped by the heart. The valves thereby allow only a unidirectional flow of blood through the lumen or passageway of the heart valve. The annular body is suspended within a stiffening ring and a locking wire of a predetermined diameter is contained within annular grooves formed in the outer surface of the annular body and the inner surface of the stiffening ring to prevent longitudinal movement of the annular body relative to the stiffening ring.

A fabric sewing cuff encompasses the outer surfaces of the stiffening ring. Disposed between a portion of the fabric sewing cuff and the stiffening ring is a moisture-proof, annular container for housing an electronic sensor, as well as a printed circuit board populated with appropriate electronic components for implementing a RF transceiver and an appropriate active or passive power supply for energizing same.

The sensor may comprise any one of a number of types capable of detecting the motion of the occluder and for providing an electrical signal indicative thereof to the transceiver circuitry. A blood flow sensor may also be used. The transceiver then functions to transmit analog or digital information to a suitable monitor located outside of the body of the patient in which the valve of the present invention is implanted. This sensor, in detecting the motion of the leaflets, may function to detect blood flow, cardiac output, as well as certain other information indicative of the function of the heart. The implanted transceiver can also receive commands from an external transmitter to accomplish some physiologic function, such as providing cardiac stimulating pulses in the event that post-surgical heart block occurs, or alternatively to control other cardiac arrhythmias.

DESCRIPTION OF THE DRAWINGS

The foregoing features, objects and advantages of the invention will become apparent to those skilled in the art from the following detailed description of the preferred embodiment, especially when considered in conjunction with the accompanying drawings in which like numerals in the several views refer to corresponding parts.

DESCRIPTION OF THE PREFERRED EMBODIMENT

Figure 1:
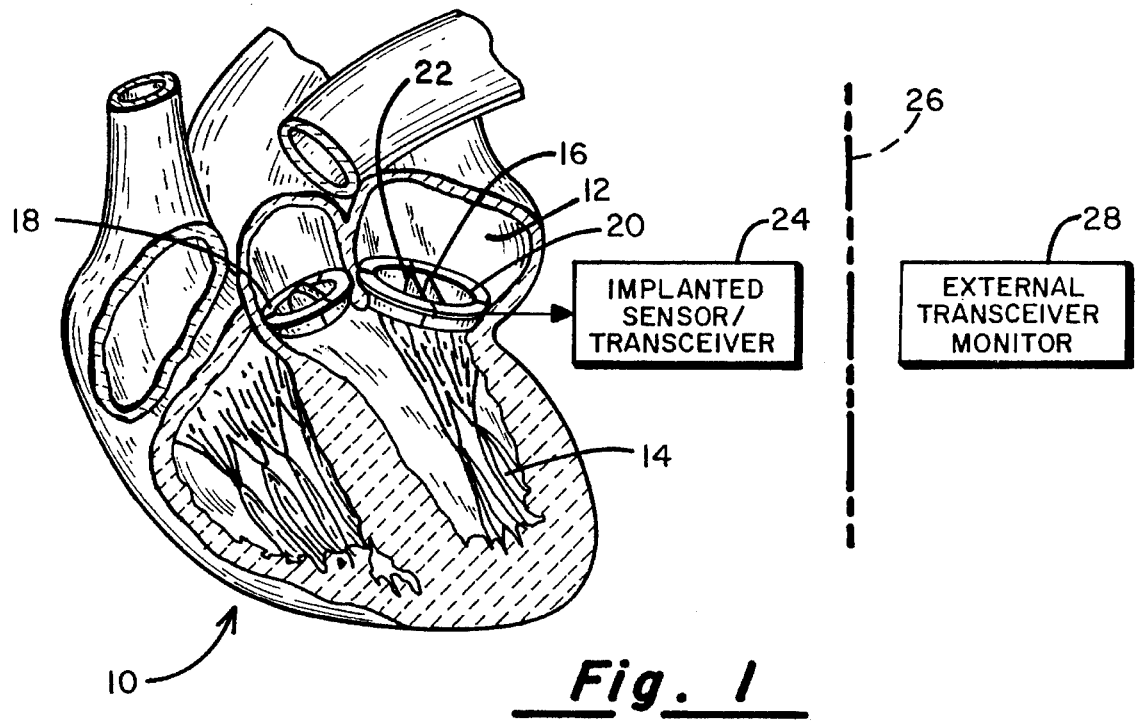
FIG. 1 illustrates a cross-section through the heart illustrating heart valve prostheses in accordance with the present invention used as replacements for the mitral valve and an aortic valve.

For purposes of reference only, there is shown in FIG. 1 a vertically sectioned human heart 10 showing the right atrium 12, the left ventricle 14 and an artificial heart valve prosthesis 16 replacing the normal mitral valve and a further prosthetic heart valve 18 replacing the subject's aortic valve. The present invention may also be incorporated in a prosthesis replacing the tricuspid valve.

As will be explained in greater detail hereinbelow, either or both of the heart valve prostheses 16 and 18 may incorporate therein an appropriate sensor positioned and configured to detect the normal movement of the leaflets 20 and 22 as they open and close under influence of the blood flowing through the annular body of the artificial heart valve 16. The sensor module 24 is preferably contained within the valve structure, as will be further described, but in accordance with another feature of the present invention, the transceiver electronics may be in a separate moisture-proof container and coupled to the heart valve 16 in such a way that it can receive, amplify and transmit information transcutaneously through the chest wall 26 to an external transceiver/monitor 28.

Figure 2:
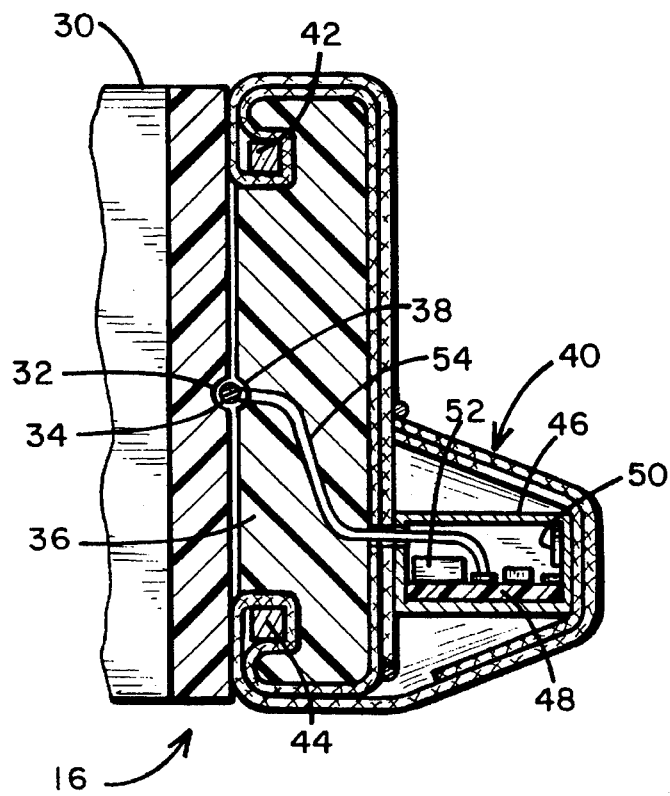
FIG. 2 is a greatly enlarged partial cross-sectional longitudinal view showing an electronics module contained within the sewing cuff of a typical heart valve prosthesis for transmitting and receiving information and commands transcutaneously to an external monitor system.
Figure 2:
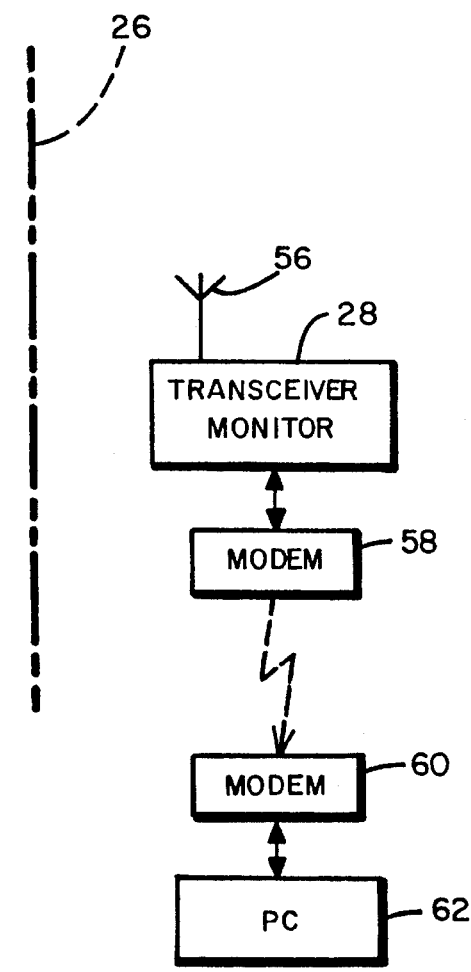

Referring next to FIG. 2, the heart valve 16 is seen to include an annular body member 30 preferably formed from, but not limited to, pyrolytic carbon in which the occluder or leaflets 20 and 22 are pivotally suspended. The view of FIG. 2 does not show the leaflets themselves. As is fully explained in the aforereferenced co-pending application, the outer peripheral surface of the annular body 30 includes a groove 32 for receiving a lock wire 24 therein. Surrounding the valve body 30 is a metal or plastic stiffening ring 36 which also has an annular groove 38 formed therein for receiving a portion of the lock wire 34 therein. Stiffening ring 36 may be constructed of a non-conductive material. The tolerances are such that the lock wire 34 prevents relative longitudinal sliding motion between the annular body 30 and its surrounding stiffening ring 36.

Also formed inwardly of the annular surface of the stiffening ring 36 are upper and lower grooves designed to contain and trap a fabric sewing cuff 40 are first and second lock rings 42 and 44. Because of the manner in which the fabric sewing cuff 40 is wrapped about the stiffening ring 36 and the lock rings 42 and 44, the sewing cuff is prevented from coming free of the assembled heart valve 16.

In the embodiment of the heart valve disclosed in the aforereferenced '802 application, a plastic filler ring, identified therein by numeral 58, is fitted between the exterior of the stiffening ring 36 and the sewing cuff to create an annular flange. In the embodiment shown in FIG. 2 hereof, the filler ring is replaced by a moisture-proof ring-shaped container or housing 46, which is preferably a welded titanium can designed to house the circuitry identified by numeral 24 in FIG. 1. The cross-sectional view of FIG. 2 shows within can 46 a printed circuit substrate 48 which is populated with integrated and discrete electronic components comprising a transceiver circuit. A printed circuit coil antenna 50 is coupled to the electronic circuitry on the printed circuit board 48 for transmitting and receiving electrical signals.

Also housed within the container 46 is a suitable sensor element 52. The sensor 52 may be capacitive or inductive in nature and appropriately arranged to sense the movement of the leaflets 20 and 22 (FIG. 1). An inductive transducer may comprise a coil positioned in the stiffening ring to be cut by magnetic flux from a dipole mounted on or in the occluder. Those skilled in the art can appreciate that other forms of transducers for detecting movement and/or fluid flow through the annular body 30 can also be utilized in carrying out the principles of the present invention. For example, an ultrasonic Doppler flow sensor may be used to detect the behavior of the blood flow through the valve body as the leaflets open and close. Also, a quartz crystal transducer can be employed to sense vibration.

A suitable active power source, such as a lithium iodide battery of the type used in cardiac pacemakers may also be contained within the housing 46. Alternatively, a passive power source comprising the antenna 50 coupled through a suitable diode rectifying circuit to an energy storing capacitor may be provided so that the electronics within the housing 46 can be powered by a continuous wave RF signal transmitted percutaneous from the transceiver/monitor circuit 28 to the implanted valve electronics percutaneously.

When it is considered that the AV node, which controls the rate of the ventricles, is located in close proximity to both the mitral valve and the aortic valve and given the fact that during the post-operative period it is not uncommon for a patient to go into temporary or permanent heart block, it is also desirable that a means be provided for pacing the heart. In the past, it has been the practice to install temporary pacing leads percutaneously for connection to an external pacemaker. The heart pacing leads are relatively costly and require a channel through the skin which can become a site for infection, requiring ultimate removal of the leads.

Because the lock wire 32 is a conductor and is in blood contact, by connecting that wire to an electronic pulse generator within the housing 46 and controlling the pulse generator through an RF link between the antenna 56 of transceiver 28 and the antenna 50 of the implanted transceiver, pacing of the ventricles can be achieved.

In monitoring the operation of the implanted heart valve, information telemetered from the implanted electronics module to the external transceiver/monitor 28 allows assessment of such things as leaflet movement, pannus overgrowth on the ring, cardiac arrhythmias, cardiac output.

If it is desired to be able to assess a patient at a distance, the transceiver 28 located proximate the patient may be coupled, via modems 58 and 60, to a remotely located personal computer 62 located, for example, in the office of the cardiac surgeon, cardiologist, or paramedical personnel.

Figure 3:
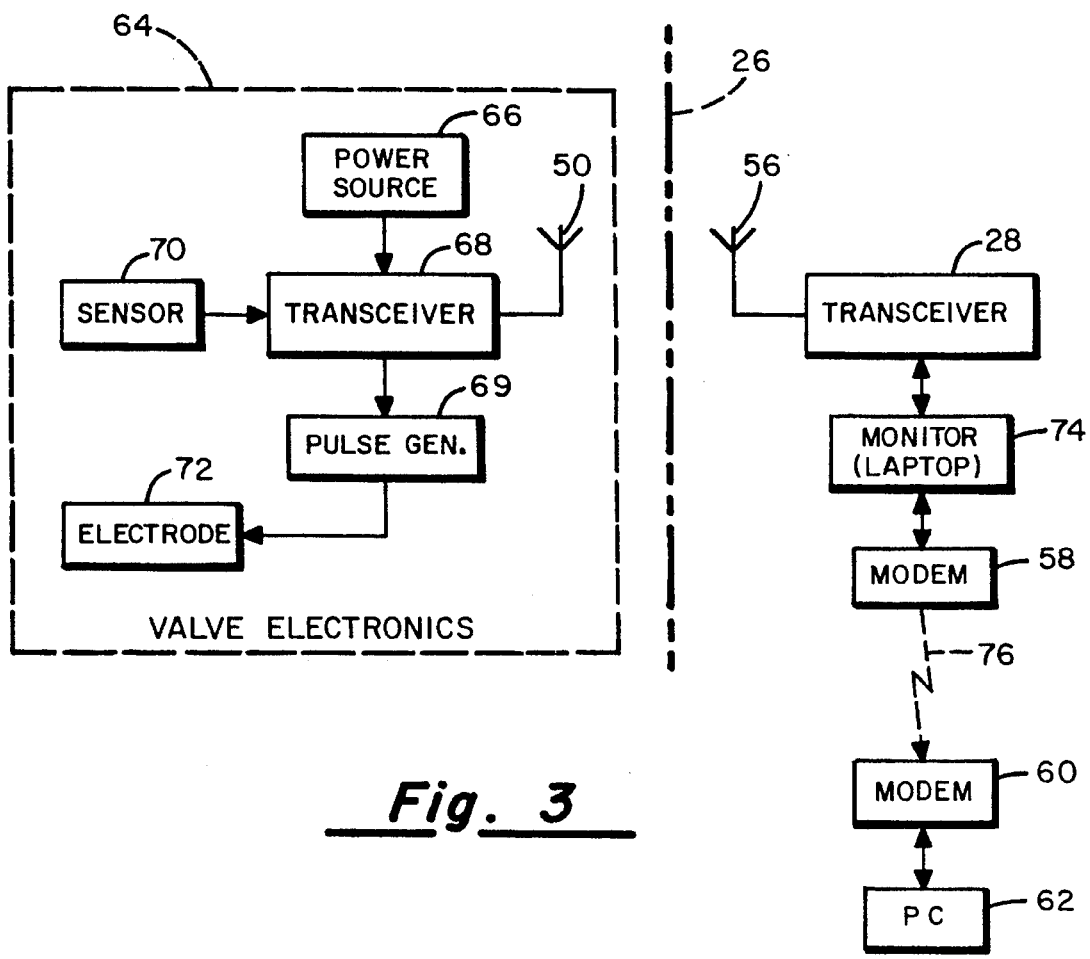
FIG. 3 is a block diagram of the electronics associated with the heart valve prosthesis in accordance with the present invention.

FIG. 3 is a system block diagram showing the implanted electronics within the broken line box 64. As earlier mentioned, the implanted electronic components may be contained as an integral part of the heart valve in the manner illustrated in FIG. 2 or, alternatively, the power source 66 and transceiver 68 may be separately packaged within a moisture-proof housing external to the heart but still within the patient's chest area. Only the sensor 70 and the electrode 72 would be disposed on or in the prosthetic heart valve itself. As before, messages may be transmitted percutaneously through the chest wall 26 to a local transceiver 28 and monitor 74 which may be a lap-top computer or similar device programmed to analyze the information provided by the sensor 70 to the implanted transceiver 68 and transmitted thereby to the transceiver 28. By using modems 58 and 60 joined to a telephone link 76, it is possible to monitor/control operation of the system from a remote location.

In the event an arrhythmia is detected, the system can be programmed to automatically initiate cardiac pacing. The monitor 74 will provide command pulses at a predetermined pacing rate to the transceiver 28 which will then send a command to the implanted transceiver 68 so that it can control the application of cardiac stimulating pulses from the pulse generator 69 to the electrode 72. As mentioned in connection with FIG. 2, the electrode 72 may comprise the lock wire 34 forming a part of the heart valve itself.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

For example, rather than disposing the electronics module in a moisture-proof container located between the sewing cuff 40 and the stiffening ring 36, some or all of the components comprising the electronics module may also be embedded in the stiffening ring 36. Hence the scope of the invention is to be determined from the following claims, when properly interpreted in light of the prior art.

What is claimed is:

1. In combination, an artificial heart valve of the type having a tubular body member, defining a lumen and pivotally supporting at least one occluder, said body member having a sewing cuff covering an exterior surface of said body member; and an electronic sensor module disposed between said sewing cuff and said exterior surface, wherein said sensor module incorporates a sensor element for detecting movement of said at least one occluder between an open and a closed disposition relative to said lumen and wherein said sensor module further includes a signal transceiver coupled to said sensor element, and means for energizing said signal transceiver, and wherein said sensor module includes means for encapsulating said sensor element, signal transceiver and energizing means in a moisture-impervious container.

2. In combination, an artificial heart valve of the type having a tubular body member, defining a lumen and pivotally supporting at least one occluder, said body member having a sewing cuff covering an exterior surface of said body member; and an electronic sensor module disposed between said sewing cuff and said exterior surface, wherein said sensor module further includes a signal transceiver coupled to said sensor element, and means for energizing said signal transceiver.

3. The combination as in claim 2 wherein said sensor module incorporates a sensor element for detecting movement of said at least one occluder between an open and a closed disposition relative to said lumen.

4. In combination, an artificial heart valve of the type having a tubular body member defining a lumen and pivotally supporting at least one occluder, said body member having a sewing cuff covering an external surface of said body member; an electrode disposed on said tubular body member; a transceiver module including a moisture impervious housing, said housing containing an electronic transceiver having an output coupled to said electrode, and means located remote from said electronic transceiver for transmitting pulses for pacing cardiac tissue to said electronic transceiver.

5. The combination as in claim 4 wherein said means for transmitting pulses comprises a radio-telemetry device.

6. The combination as in claim 4 wherein said moisture impervious housing is disposed between said sewing cuff and said body member.

7. The combination as in claim 5 wherein said radio-telemetry device is external to the body in which said heart valve is implanted.

8. An apparatus for telemetering information on the operating characteristics of an implanted heart valve of the type including at least one occluder mounted within a valve body member to a location external to the patient, comprising:

(a) means disposed on said implanted heart valve for sensing movement of said occluder relative to said valve body and producing a first electrical signal indicative of such movement;

(b) a transceiver means and a source of electrical energy coupled thereto disposed within a moisture-impervious housing and with said transceiver means being operatively coupled to said sensing means for receiving said first electrical signal and for producing a second electrical signal capable of percutaneous electronic transmission of information related to said first electrical signal from said housing to a location external to the patient in which said artificial heart valve is implanted; and (c) monitoring means external to the body of the patient for receiving and analyzing said information.

9. The apparatus as in claim 8 wherein said sensing means senses capacitive changes resulting from movement of said occluder.

10. The apparatus as in claim 8 wherein said sensing means senses inductive changes resulting from movement of said occluder.

11. The apparatus as in claim 8 wherein said sensing means senses vibration of said body member resulting from movement of said occluder.

12. The apparatus as in claim 8 wherein said sensing means is not disposed in a blood path passing through said body member.

13. In combination, an artificial heart valve of the type having a tubular body member, defining a lumen and pivotally supporting at least one occluder, said body member having a sewing cuff covering an exterior surface of said body member; and an electronic sensor module disposed between said sewing cuff and said exterior surface, wherein said sensor module incorporates a sensor element for detecting movement of said at least one occluder between an open and a closed disposition relative to said lumen, and further including an implantable transceiver module, said transceiver module comprising a radio-telemetry circuit operatively coupled to said sensor element for receiving an input signal therefrom relating to the detected movement of said at least one occluder and for providing an output signal to an antenna.

14. The combination as in claim 13 wherein said implantable transceiver module is external to said artificial heart valve.

15. The combination as in claim 13 and further including electrode means incorporated into said artificial heart valve and coupled to said transceiver module for stimulating heart tissue upon receipt of heart pacing signals from an exterior transceiver via said antenna.

16. The combination as in claim 13 wherein said transceiver module further includes means for energizing said radio-telemetry circuit and said sensor element.

17. The combination as in claim 16 wherein said sensor element comprises a capacitance element.

18. The combination as in claim 16 wherein said sensor element comprises an inductance element.

19. The combination as in claim 16 wherein said sensor element comprises a vibration sensor.

20. The combination as in claim 19 wherein said vibration sensor is a quartz crystal.

\* \* \* \* \*